United States Patent [19]
Jonczyk et al.

[11] Patent Number: 6,001,961
[45] Date of Patent: *Dec. 14, 1999

[54] CYCLIC ADHESION INHIBITORS

[75] Inventors: Alfred Jonczyk; Simon Goodman; Beate Diefenbach; Arne Sutter, all of Darmstadt; Günter Hölzemann, Seeheim; Horst Kessler; Michael Dechantsreiter, both of Garching, all of Germany

[73] Assignee: Merck Patent Gesellschaft mit Beschrankter Haftung, Darmstadt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/694,387

[22] Filed: Sep. 16, 1996

[30] Foreign Application Priority Data

Sep. 15, 1995 [DE] Germany ............................ 195 34 177

[51] Int. Cl.$^6$ ...................................................... C07K 7/00
[52] U.S. Cl. ......................... 530/317; 530/330; 530/338; 514/9; 514/11
[58] Field of Search ................................... 530/317, 330, 530/338; 514/9, 11

[56] References Cited

U.S. PATENT DOCUMENTS

| | | | |
|---|---|---|---|
| 4,508,921 | 4/1985 | Amato et al. | 562/443 |
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacker et al. | 623/11 |
| 4,792,525 | 12/1988 | Ruoslahti et al. | 435/240.243 |
| 5,849,692 | 12/1998 | Jonczyk et al. | 514/11 |

FOREIGN PATENT DOCUMENTS

| | | |
|---|---|---|
| 406 428 | 1/1991 | European Pat. Off. . |
| 4310643 | 10/1994 | Germany . |

OTHER PUBLICATIONS

Aumailley et al., "Strong and selective inhibitors of cell adhesion . . . ", FEBS Letters, vol. 291, No. 1, Oct. 1991, pp. 50–54.

Jackson et al., *J. Am. Chem. Soc.*, 116(8), pp. 3220–3230, 1994.

Coy et al., *Tetrahedron*, 44(3), 835–41, 1988.

*Primary Examiner*—Michael P. Woodward
*Assistant Examiner*—C. Delacroix-Muirheid
*Attorney, Agent, or Firm*—Millen, White, Zelano & Branigan, P.C.

[57] ABSTRACT

The invention relates to novel cyclopeptides of the formula I $$\text{cyclo-(nArg-nGly-nAsp-nD-nE)} \qquad \text{I,}$$

in which

D and E in each case independently of one another are Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homo-Phe, Phg, Pro, Pya, Ser, Thr, Tia, Tic, Trp, Tyr or Val, which amino acid residues can also be derivatized, R is alkyl having 1–18 carbon atoms, Hal is F, Cl, Br, I, Ac is alkanoyl having 1–10 carbon atoms, aroyl having 7–11 carbon atoms or aralkanoyl having 8–12 carbon atoms, n denotes no substituent or an alkyl radical R, benzyl or an aralkyl radical having 7–18 carbon atoms on the alpha-amino function of the relevant amino acid residue, with the proviso that at least one amino acid residue has a substituent n and that, where residues of optically active amino acids and amino acid derivatives are involved, both the D and the L forms are included, and also their physiologically acceptable salts.

These compounds act as integrin inhibitors and can be used in particular for the prophylaxis and treatment of disorders of the circulation, angiogenic disorders, microbial infections and in tumor therapy.

5 Claims, No Drawings

CYCLIC ADHESION INHIBITORS

SUMMARY OF THE INVENTION

The invention relates to novel cyclopeptides of the formula I cyclo-(nArg-nGly-nAsp-nD-nE)   I, in which
  D and E in each case independently of one another are Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homo-Phe, Phg, Pro, Pya, Ser, Thr, Tia, Tic, Trp, Tyr or Val, which amino acid residues can also be derivatized,
  R is alkyl having 1–18 carbon atoms,
  Hal is F, Cl, Br, I,
  Ac is alkanoyl having 1–10 carbon atoms, aroyl having 7–11 carbon atoms or aralkanoyl having 8–12 carbon atoms,
  n denotes no substituent or is an alkyl radical R, benzyl or an aralkyl radical having 7–18 carbon atoms on the alpha-amino function of the relevant amino acid residue, with the proviso that at least one amino acid residue has a substituent n and that, where residues of optically active amino acids and amino acid derivatives are involved, both the D and the L forms are included, and also their physiologically acceptable salts.

Similar compounds, but having no N-alkylation, are known from, for example, EP 0 406 428 and FEBS Lett. 291, 50–54 (1991).

An object of the invention was to discover novel compounds having valuable properties, especially those which can be used for the production of medicaments, in analogy to the compounds in EP 0406 428 and FEBS Lett. 291, pp. 50–54.

It has surprisingly been found that the compounds of the formula I and their salts possess very valuable properties. In particular, they act as integrin inhibitors, in which context they inhibit in particular the interactions of β$_3$- or β$_5$-integrin receptors with ligands. The compounds are particularly active in the case of the integrins a$_V$β$_3$, a$_V$β$_5$ and a$_{IIb}$β$_3$, but also relative to a$_V$β$_1$-, a$_V$β$_6$- and a$_V$β$_8$ receptors. These actions can be demonstrated, for example, according to the method described by J. W. Smith et al. in J. Biol. Chem. 265, 12267–12271 (1990). In addition, the compounds possess anti-inflammatory effects.

The dependency of the development of angiogenesis on the interaction between vascular integrins and extra-cellular matrix proteins is described by P. C. Brooks, R. A. Clark and D. A. Cheresh in Science 264, 569–71 (1994).

The possibility of inhibiting this interaction and the associated initiation of apotosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I which block the interaction of integrin receptors and ligands, for example of fibrinogen to the fibrinogen receptor (glycoprotein IIb/IIIa), act as GPIIb/IIIa antagonists in preventing or lessening the propagation of tumor cells by metastasis. This is demonstrated by the following observations:

The compounds are able to inhibit the binding of metalloproteinases to integrines and therefore interfere with the cells' use of the enzymatic activity of the proteinases. This is for example described by the inhibition of the binding from matrix metalloproteinase-2 (MMP-2) to the vitronektion receptor α$_V$β$_3$ by a cyclic RGD peptide in Cell 85, 683–693 (1996) by P. C. Brooks et al.

The propagation of tumor cells from a local tumor into the vascular system takes place via the formation of microaggregates (microthrombi) by interaction of the tumor cells with blood platelets. The tumor cells are screened by the protection afforded in the microaggregates, and are not recognized by the cells of the immune system.

The microaggregates are able to settle on vessel walls, facilitating the further penetration of tumor cells into the tissue. Since the formation of the microthrombi is mediated by binding of fibrinogen to the fibrinogen receptors on activated blood platelets, the GPIIa/IIIb antagonists can be regarded as effective inhibitors of metastasis.

The compounds of the formula I can also be employed as antimicrobial substances in the case of operations where biomaterials, implants, catheters or pacemakers are employed. In this context they have an antiseptic action. The effectiveness of the antimicrobial activity can be demonstrated by the method described by P. Valentin-Weigund et al., in Infection and Immunity, 2851–2855 (1988).

Since the compounds of the formula I constitute inhibitors of fibrinogen binding and thus ligands of the fibrinogen receptors on blood platelets, they can be used in vivo in the vascular system as diagnostic agents for the detection and location of thrombi, provided that they are substituted by a isotope-marked or UV-detectable radical. In picture-producing methods it is possible to detect and localize tumors in an organism (tumor imaging, PET).

The compounds of the formula I, as inhibitors of fibrinogen binding, can also be used as effective aids in studying the metabolism of blood platelets in different activation stages or of intracellular signal mechanisms of the fibrinogen receptor. The detectable unit of an incorporated label, for example biotinyl, after binding to the receptor, enables said mechanisms to be investigated.

The compounds therefore have the property of inhibiting the binding of natural or synthetic ligands to integrins, especially the integrins α$_V$β$_3$, α$_V$β$_5$ and α$_{IIb}$β$_3$, but also of α$_V$β$_1$, α$_V$β$_6$ and α$_V$β$_8$.

Moreover, they have the advantage over the prior art that N-alkylation of one or more peptide linkages brings about metabolic stabilization and increased fat-solubility. Through the reduction in possible hydrogen bridges, since N-alkyl cannot be an H donor for C=O, the capacity to penetrate membranes is improved, so that it is possible to obtain increased oral absorbability; moreover, increased plasma protein binding may occur.

The N-alkylation of the peptide linkage increases the inhibitory potency of the compounds and raises the selectivity of the inhibition in respect of specific integrins. The selectivity can be influenced in particular by the position and number of the N-alkyl groups.

The compounds can be employed as pharmaceutically active principles in human and veterinary medicine, in particular for the prophylaxis and treatment of disorders of the circulation, thrombosis, cardiac infarction, arteriosclerosis, inflammations, apoplexy, angina pectoris, tumor disorders, osteolytic disorders, especially osteoporosis, angiogenesis and disorders resulting from angiogenesis, for example diabetic retinopathy of the eye, macular degeneration, myopia, ocular histoplasmosis, rheumatic arthritis, osteoarthritis, rubeotic glaucoma, and also ulcerative colitis, Crohn's disease, multiple sclerosis, psoriasis and restenosis following angioplasty. The compounds may additionally be used to improve and support wound healing processes in the case of microbial infections and in acute renal failure.

These actions can be demonstrated, for example, with the aid of methods known from the literature, as described for example by P. C. Brooks et al. in Cell. 79, 1157–1164 (1994) or Science 264, 569–571 (1994).

The abbreviations of amino acid residues shown above and below represent the residues of the following amino acids:

| | |
|---|---|
| Abu | 4-aminobutyric acid |
| Aha | 6-aminohexanoic acid |
| Ala | alanine |
| Asn | asparagine |
| Asp | aspartic acid |
| Asp(OR) | aspartic acid (β ester) |
| Arg | arginine |
| Cha | 3-cyclohexylalanine |
| Cit | citrulline |
| Cys | cysteine |
| Dab | 2,4-diaminobutyric acid |
| Dap | 2,3-diaminopropionic acid |
| Gln | glutamine |
| Glu | glutamic acid |
| Gly | glycine |
| His | histidine |
| Ile | isoleucine |
| Leu | leucine |
| Lys | lysine |
| Lys (Ac) | Nε-alkanoyllysine |
| Lys (AcNH$_2$) | Nε-aminoalkanoyllysine |
| Lys (AcSH) | Nε-mercaptoalkanoyllysine |
| Met | methionine |
| Nal | 3-(2-naphthyl)alanine |
| Nle | norteucine |
| Orn | ornithine |
| Phe | phenylalanine |
| 4-Hal-Phe | 4-halophenylalanine |
| Phg | phenylglycine |
| Pro | proline |
| Pya | 3-(2-pyridyl)alanine |
| Sar | sarcosine (N-methylglycine) |
| Ser | serine |
| Tia | 3-(2-thienyl)alanine |
| Tic | tetrahydroisoquinoline-3-carboxylic acid |
| Thr | threonine |
| Trp | tryptophan |
| Tyr | tyrosine |
| Val | valine. |

In addition, the meaning of the following abbreviations is as follows:

| | |
|---|---|
| BOC | tert-butoxycarbonyl |
| Bzl | benzyl |
| DCCI | dicyclohexylcarbodiimide |
| DMF | dimethylformamide |
| EDCI | N-ethyl-N'-(3-dimethylaminopropyl)-carbodiimide hydrochloride |
| Et | ethyl |
| Fmoc | 9-fluorenylmethoxycarbonyl |
| HOBt | 1-hydroxybenzotriazole |
| Me | methyl |
| Mtr | 4-methoxy-2,3,6-trimethylphenylsulfonyl |
| NMe | N-methylated α-amino group |
| OBut | tert-butyl ester |
| OMe | methyl ester |
| OEt | ethyl ester |
| POA | phenoxyacetyl |
| iPr | isopropyl |
| nPr | n-propyl |
| TBTU | 2-(1H-benzotriazol-1-yl)-1,1,3,3 tetramethyluronium tetrafluoroborate |
| TFA | trifluoroacetic acid. |

Where the above-mentioned amino acids can occur in a number of enantiomeric forms, then all of these forms and also their mixtures (e.g. the DL forms) are included above and below, for example as constituents of the compounds of the formula I. The amino acids, for example as a constituent of compounds to the formula I, can also be provided with appropriate protecting groups which are known per se.

In addition, the invention also includes those peptides whose amino acid residues are fully or partially derivatized. The term "derivatized" is to be understood such that so-called "prodrugs", for example N-guanidino-acylderivatives of Arg, β-esters of Asp, Nε-alkanoyl, Nε-aminoalkanoyl and Nε-mercaptoalkanoyl derivatives of lysine, to name but a few, are also included. In addition, the amino acid residues can in part be C-alpha-alkylated or, for example for diagnostic purposes, can be isotope-labeled. Also included are those compounds of the formula I which in the side chains of the units D and E are additionally derivatized by amino, carboxyl or mercapto groups, since such derivatives are important starting compounds for the preparation of conjugates of higher molecular weight, for example for immunization purposes and antibody production. It is additionally possible to use functional groups in the side chain of certain amino acid residues such as —COOH (e.g., in Asp or Asn) or —NH$_2$ (e.g., in Lys) or —OH (e.g., in Ser) of derivatized amino acid residues to immobilize the peptides on polymer materials for the production of affinity chromatography columns, or to utilize the functional groups for derivatization with diagnostic auxiliary reagents, such as fluorescent substituents.

The invention additionally relates to a process for the preparation of a compound of the formula I according to claim 1 or one of its salts, characterized in that it is liberated from one of its functional derivatives by treatment with a solvolysing or hydrogenolyzing agent or in that a peptide of the formula II

in which
Z-nArg-nGly-nAsp-nD-nE-nGly-nAsp-nD-nE-nArg-nAsp-nD-nE-nArg-nGly-nD-nE-nArg-nGly-nAsp or-nE-nArg-nGly-nAsp-nD-, or a reactive derivative of such a peptide, is treated with a cyclizing agent, or in that a cyclopeptide which corresponds per se to the formula I but which has one or more free amino groups, acid groups and/or activated α carbon atoms is derivatized by alkylation, acylation or esterification.

and/or in that a basic or acidic compound of the formula I is converted into one of its salts by treatment with an acid or base.

Above and below, the radicals D, E and n have the meanings given in the case of the formulae I and II unless expressly stated otherwise. The letters used for the respective radicals have nothing to do with the single-letter code for amino acids.

In the above formulae, alkyl is preferably methyl, ethyl, isopropyl, n-butyl, sec-butyl or tert-butyl.

The group D is preferably Phe, also preferably D-Phe, but also 4-Hal-Phe, especially 4-I-Phe and Trp, Tyr, homo-Phe, Nal or Phg, the D forms also being equally preferred.

E is preferably a hydrophobic amino acid residue, especially Gly, Ala, Val, Leu, Nle or Ile. The variable n is preferably N-methyl-, N-ethyl-, N-propyl-, N-benzyl- or N-isopropyl- substituted α-amino groups in the peptide, it being possible for two or more amino acid residues to be N-substituted by identical or different alkyl radicals.

Accordingly, the invention relates in particular to those compounds of the formula I in which at least one of the radicals mentioned has one of the above-mentioned preferred meanings.

A preferred group of compounds can be expressed by the subformula Ia, which otherwise corresponds to the formula I but in which D is D-Phe, Phe, D-Trp, Trp, D-Tyr, Tyr, D-homoPhe, homoPhe, D-Nal, Nal, D-Phg, Phg or 4-Hal-Phe (D or L form), and E is Val, Gly, Ala, Leu, Ile or Nle.

Another preferred group of compounds can be expressed by the subformula Ib, which otherwise corresponds to the formula I but in which D is D-Phe and E is Gly, Ala, Val, Leu, Ile or Nle, and one of the amino acid residues Arg, Gly or Asp has an alkyl substituent on the α-amino group.

A further preferred group of compounds can be expressed by the subformula Ic, which corresponds to the subformulae Ia and Ib and to the formula I but in which one of the amino acid residues D or E is alkylated on the α-amino group.

Furthermore, particular preference is given to all physiologically compatible salts of the compounds which come under the subformulae Ia, Ib and Ic.

The compounds of the formula I and also the starting materials for their preparation are, moreover, prepared by known methods, as are described in the literature (for example in the standard works such as Houben-Weyl, Methoden der organischen Chemie [Methods of Organic Chemistry], Georg-Thieme-Verlag, Stuttgart), in particular under reaction conditions which are known and appropriate for the said reactions. In this context, use can also be made of known variants which are not mentioned in any greater detail here.

If desired, the starting substances can also be formed in situ, so that they are not isolated from the reaction mixture but are immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which contain appropriate protected amino and/or hydroxyl groups instead of one or more free amino and/or hydroxyl groups, preferably those which carry an amino protecting group instead of a hydrogen atom which is attached to a nitrogen atom, examples being those which correspond to the formula I but which, instead of an $NH_2$ group, contain an NHR' group (where R' is an amino protecting group, e.g. BOC or CBZ).

Other preferred starting materials are those which carry a hydroxyl protecting group instead of the hydrogen atom of a hydroxyl group, for example those which correspond to the formula I but contain, instead of a hydroxyphenyl group, a R" O-phenyl group (where R" is a hydroxyl protecting group as defined below).

It is also possible for two or more—identical or different—protected amino and/or hydroxyl groups to be present in the molecule of the starting material. If the protecting groups present are different from one another, then in many cases they can be eliminated selectively.

The expression "amino protecting group" is generally known and relates to groups which are suitable for protecting (for blocking) an amino group from chemical reactions but which are readily removable after the desired chemical reaction has been carried out at other positions of the molecule. Typical of such groups are, in particular, unsubstituted or substituted acyl, aryl, aralkoxymethyl or arakyl groups. Since the amino protecting groups are removed after the desired reaction (or reaction sequence), their nature and size is otherwise not critical; however, preference is given to those having 1–20, in particular 1–8, carbon atoms. The term "acyl group" is to be interpreted in its widest sense in connection with the present process. It includes acyl groups derived from aliphatic, araliphatic, aromatic or heterocyclic carboxylic acids or sulfonic acids and, in particular, alkoxycarbonyl, aryloxycarbonyl and, above all, aralkoxycarbonyl groups. Examples of such acyl groups are alkanoyl such as acetyl, propionyl, butyryl; aralkanoyl such as phenylacetyl; aroyl such as benzoyl or toluoyl; aryloxyalkanoyl such as POA; alkoxycarbonyl such as methoxycarbonyl, ethoxycarbonyl, 2,2,2-trichlorethoxy-carbonyl, BOC, 2-iodoethoxycarbonyl; aralkyloxycarbonyl such as CBZ ("carbobenzoxy"), 4-methoxybenzyloxy-carbonyl, FMOC; and arylsulfonyl such as Mtr. Preferred amino protecting groups are BOC and Mtr, and also CBZ, Fmoc, benzyl and acetyl.

The expression "hydroxyl protecting group" above is also generally known and relates to groups which are suitable for protecting a hydroxyl group from chemical reactions but which are readily removable after the desired chemical reaction has been carried out at other positions of the molecule. Typical of such groups are the above-mentioned unsubstituted or substituted aryl, aralkyl or acyl groups, and also alkyl groups. The nature and size of the hydroxyl protecting groups is not critical, since they are removed again after the desired chemical reaction or reaction sequence; preference is given to groups having 1–20, especially 1–10, carbon atoms. Examples of hydroxyl protecting groups include benzyl, p-nitrobenzoyl, p-toluenesulfonyl, tert-butyl and acetyl, with particular preference being given to benzyl and tert-butyl. The COOH groups in aspartic acid and glutamic acid are preferably protected in the form of their tert-butyl esters (e.g. Asp(OBut)).

The functional derivatives of the compounds of the Formula I which are to be used as starting materials can be prepared by customary methods of amino acid and peptide synthesis, as are described, for example, in the patent applications and standard works mentioned, including for example by the solid-phase method according to Merrifield (B. F. Gysin and R. B. Merrifield, J. Am. Chem. Soc. 94, 3102 ff. (1972)).

The liberation of the compounds of the formula I from their functional derivatives is carried out—depending on the protecting group used—with, for example, strong acids, expediently with TFA or perchloric acid, but also with other strong inorganic acids, such as hydrochloric acid or sulfuric acid, strong organic carboxylic acids, such as trichloroacetic acid, or sulfonic acids such as benzene- or p-toluenesulfonic acid. The presence of an additional inert solvent is possible but not always necessary. Suitable inert solvents are preferably organic, for example carboxylic, acids such as acetic acid, ether such as tetrahydrofuran or dioxane, amides such as DMF, halogenated hydrocarbons such as dichloromethane, and also alcohols such as methanol, ethanol or isopropanol, and water. Also suitable are mixtures of the above-mentioned solvents. TFA is preferably used in excess without the addition of a further solvent, perchloric acid is preferably used in the form of a mixture of acetic acid and 70% perchloric acid in a ratio of 9:1. The reaction temperatures for the cleavage are expediently between about 0 and about 50°; it is preferably carried out between 15 and 30° (room temperature).

The groups BOC, OBut and Mtr can be removed, for example, preferably using TFA in dichloromethane or with about 3 to 5 N HCl in dioxane at 15–30°, while the FMOC group can be eliminated with an approximately 5 to 50% solution of dimethylamine, diethylamine or piperidine in DMF at 15–30°.

Protecting groups which can be removed by hydrogenolysis (e.g. CBZ or benzyl) can be eliminated, for example, by treatment with hydrogen in the presence of a catalyst (e.g. a noble metal catalyst such as palladium, preferably on a support such as charcoal). Suitable solvents in this context are those mentioned above, especially, for example, alcohols such as methanol or ethanol or amides such as DMF. The hydrogenolysis is carried out, as a rule, at temperatures between about 0 and 100° and at pressures of between about 1 and 200 bar, preferably at 20–30° and 1–10 bar. Hydrogenolysis of the CBZ group, for example, takes place readily on 5 to 10% Pd-C in methanol or using ammonium formate (instead of $H_2$) on Pd-C in methanol/DMF at 20–30°.

Compounds to the formula I can also be obtained by cyclization of compounds of the formula II under the conditions of a peptide synthesis. In this case, the reaction is expediently carried out in accordance with customary methods of peptide synthesis as described, for example, in Houben-Weyl, l.c., Volume 15/II, Pages 1 to 806 (1974).

The reaction is preferably carried out in the presence of a dehydrating agent, for example a carbodiimide such as DCCI or EDCI, and additionally propane phosphonic anhydride (cf. Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures between about −10 and 40°, preferably between 0 and 30°. In order to promote intramolecular cyclization over intermolecular peptide bonding, it is expedient to work in dilute solutions (dilution principle).

Instead of II, suitable reactive derivatives of these substances can also be employed in the reaction, for example those in which reactive groups are intermediately blocked by protecting groups. The amino acid derivatives II can be used, for example, in the form of their activated esters which are expediently formed in situ, for example by addition of HOBt or N-hydroxysuccinimide.

In general, the starting materials of the formula II are novel. They can be prepared by known methods, for example the above-mentioned methods of peptide synthesis and of elimination of protecting groups.

In general, protected pentapeptide esters of the formula R'—Z—OR", for example BOC—Z—OMe or BOC—Z—OEt, are initially synthesized, which are first of all hydrolyzed to give acids of the formula R'—Z—OH, for example BOC—Z—OH; the protecting group R' is eliminated from these acids to give the free peptides of the formula H—Z—OH (II).

The derivatization of a cyclopeptide which corresponds per se to a compound of the formula I is likewise effected by methods known per se, as are known for the alkylation of amines, the esterification of carboxylic acids or nucleophilic substitution at aliphatic carbon atoms and are described in any textbook of organic chemistry, for example J. March, Adv. Org. Chem., John Wiley & Sons N.Y. (1985).

A base of the formula I can be converted into the associated acid addition salt using an acid. Suitable acids for this reaction are, in particular, those which yield physiologically acceptable salts. Thus inorganic acids can be used, examples being sulfuric acid, nitric acid, hydrohalic acids such as hydrochloric acid or hydrobromic acid, phosphoric acid such as orthophosphoric acid, sulfamic acid, and also organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthaline-mono- and -disulfonic acids, laurylsulfuric acid. Salts with physiologically unacceptable acids, for example picrates, can be used for isolating and/or purifying the compounds of the formula I.

Alternatively, an acid of the formula I can be converted into one of its physiologically acceptable metal or ammonium salts by reaction with a base. Particularly suitable salts in this context are the sodium, potassium, magnesium, calcium and ammonium salts, and also substituted ammonium salts, for example the dimethyl-, diethyl- or diisopropylammonium salts, monoethanol-, diethanol- or triethanolammonium salts, cyclohexylammonium salts, dicyclohexylammonium salts, dibenzylethylenediammonium salts, and also, for example, salts with N-methyl-D-glucamine or with arginine or lysine.

The novel compounds of the formula I and their physiologically acceptable salts can be used for the production of pharmaceutical preparations by bringing them into a suitable dosage form together with at least one excipient or auxiliary and, if desired, together with one or more other active principles. The preparations thus obtained can be employed as medicaments in human or veterinary medicine. Suitable excipient substances are organic or inorganic substances which are suitable for enteral (e.g. oral or rectal), parenteral (e.g. intrevenous injection) or local (e.g. topical, dermal, ophthalmic or nasal) administration or for administration in the form of an inhalation spray and which do not react with the novel compounds, examples being water or aqueous isotonic saline solution, lower alcohols, vegetable oils, benzyl alcohols, polyethylene glycols, glycerol triacetate and other fatty acid glycerides, gelatine, soya lecithin, carbohydrates such as lactose or starch, magnesium stearate, talc, cellulose and petroleum jelly. For oral application, plain tablets, coated tablets, capsules, syrups, juices or drops are particularly useful; coated tablets and capsules having enteric coatings or capsule shells are especially of interest. Suppositories are used for rectal administration, solutions for parenteral administration, preferably oily or aqueous solutions, and also suspensions, emulsions or implants. Examples of forms suitable for topical application are solutions, which can be used in the form of eye drops, and also, for example, suspensions, emulsions, creams, ointments or compresses. For administration in the form of an inhalation spray it is possible to use sprays which contain the active principle either dissolved or suspended in a propellant gas or propellant gas mixture (e.g. $CO_2$ or fluorochlorohydrocarbon substitutes). In this case the active principle is expediently used in micronized form, with the presence of one or more additional, physiologically compatible solvents, such as ethanol, being possible. Inhalation solutions can be administered with the aid of customary inhalers. The novel compounds can also be lyophilized and the resulting lypholisates used, for example, for producing injection preparations. The injections can be given as a bolus or in the form of a continuous infusion (for example intravenous, intramuscular, subcutaneous or intrathecal). The preparations stated can be sterilized and/or can comprise auxiliaries such as preservatives, stabilizers and/or wetting agents, emulsifiers, salts for influencing the osmotic pressure, buffer substances, colorants and/or flavorings. If desired they can also contain one or more other active ingredients, including for example one or more vitamins.

In general, the substances according to the invention can be administered in analogy to other known, commercially available peptides, but in particular in analogy to the compounds described in U.S. Pat. No. 4,472,305, preferably in dosages of between about 0.05 and 500 mg, in particular between 0.5 and 100 mg, per dosage unit. The daily dose is preferably between about 0.01 and 2 mg/kg of body weight. The specific dose for each particular patient depends, however, on a wide variety of factors, for example, the activity of the specific compound employed, the age, body weight, general condition of health, gender, the diet, time and route of administration, rate of excretion, combination of medicaments and severity of the particular disease to which the therapy is applied. Parenteral administration is preferred.

A compound of the present invention wherein an Arg or DArg is replaced by an Orn or DOrn may be used as a precursor for the synthesis of peptides belonging to this invention because it is possible to transfer an Orn by reaction with guanidine into an Arg. Especially this method is suitable to introduce $^{11}$C or $^{14}$C isotopes into the peptides in order to yield radioactive labeled Arg peptides.

Furthermore, the novel compounds of the formula I can be used as integrin ligands for the production of columns for affinity chromatography for the preparation of integrins in pure form.

In this case, the ligand, i.e. a peptide derivative of the formula I, is covalently coupled to a polymeric support via anchor functions.

Suitable polymeric support materials are the polymeric solid faces known in peptide chemistry, preferably having hydrophilic properties, for example crosslinked polysugars, such as cellulose, Sepharose or Sephadex®, acrylamides, polymers based on polyethylene glycol or Tentakel® polymers.

Suitable anchor functions which are linked to the polymeric supports are preferably linear alkylene chains having 2–12 carbon atoms, which are bonded directly to the polymer at one end and have a functional group, for example hydroxyl, amino, mercapto, maleimido or —COOH at the other end and are suitable for linking to the C- or N-terminal section of the respective peptide.

In this case it is possible for the peptide to be bonded directly or likewise via a second anchor function to the anchor of the polymer. It is also possible for peptides containing amino acid residues having functionalized side chains to be attached via these chains to the anchor function of the polymer.

Furthermore, certain amino acid residues, which are a constituent of the peptides of the formula I, can be modified in their side chains such that they are available for anchorage via, for example, SH, OH, $NH_2$ or COOH groups with the anchor of the polymer.

In this connection, unusual amino acids are possible, examples being phenylalanine derivatives which in position 4 of the phenyl ring carry a mercapto, hydroxyl, amino or carboxyalkyl chain, the functional group being located at the end of the chain.

Examples of amino acid residues whose side chain can be used directly as an anchor function are e.g. Lys, Orn, Arg, Dab, Dap, Asp, Asn, Glu, Gln, Ser, Thr, Cys, Cit or Tyr.

Examples of N-terminal anchors are radicals such as e.g. —CO—$C_nH_{2n}$—$NH_2$, —CO—$C_nH_{2n}$—OH, —CO—$C_n$SH or —CO—$C_nH_{2n}$—COOH where n=2–12, the length of the alkylene chain not being critical and it also being possible, if desired, for this chain to be replaced by appropriate aryl or alkylaryl radicals, for example.

C—terminal anchors can be, for example, —O—$C_nH_{2n}$—SH—, —O—$C_nH_{2n}$—OH, —O—$C_nH_{2n}$—$NH_2$, —O—$C_nH_{2n}$—COOH, —NH—$C_nH_{2n}$—SH, —NH—$C_nH_{2n}$—OH, —NH—$C_nH_{2n}$—$NH_2$ or —NH—$C_nH_{2n}$—COO, both n and the alkylene chain being subject to the comments already made in the preceding section.

The N- and C-terminal anchors can also be used as anchor component for an already functionalized side chain of an amino acid residue. Suitable amino acid residues in this case are those such as Lys(CO—$C_5H_{10}$—$NH_2$), Asp (NH—$C_3H_6$—COOH) or Cys ($C_3H_6$—$NH_2$), the anchor always being attached to the functional group of the side chain.

The materials for affinity chromatography for purifying integrins are prepared under conditions such as are customary for the condensation of amino acids and are known per se, and have already been outlined in the section for the preparation of the compounds of the formula I.

In addition to the use of cyclopeptides for immobilization on polymer materials for the production of affinity chromatography columns it is possible to utilize the compounds with their functionalized side chains for further derivatization with diagnostic auxiliary reagents, for example fluorescent substituents.

It is also possible to introduce, in addition, functional groups such as amino, mercapto or carboxyl groups into the side chains of the radicals D and E, by way of which groups it is then possible to prepare conjugates with proteins or other high molecular mass substances, for example for immunization purposes and/or antibody production.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 34 177.5, filed Sep. 15, 1995, are hereby incorporated by reference.

In the examples below, "customary working up" means: water is added if necessary, the mixture is neutralized and subjected to extraction with ether or dichloroethane, the phases are separated, the organic phase is dried over sodium sulfate, filtered and concentrated by evaporation and the residue is purified by chromatography on silica gel and/or crystallization. RT=retention time (minutes). Analysis was by HPLC on Lichrosorb® RP select B (7 μm)–250×4 mm column, Eluent A: 0.3% TFA in water; Eluent B: 0.3% TFA in 2-propanol/water (8:2) gradient 1–99% B in 50 minutes at 1 ml/min flow rate and detection at 215 nm. M+=molecular peak in the mass spectrum obtained by the "Fast Atom Bombardment" (FAB) method.

EXAMPLES

Example 1

A solution of 0.6 g of H-NMe-Arg(Mtr)-Gly-Asp(OBut)-D-Phe-Val-ONa [obtainable for example from Fmoc-NMe-Arg(Mtr)-Gly-Asp(OBut)-D-Phe-Val-O-Wang, -O-Wang being the radical of a 4-hydroxymethyl-phenoxymethyl-polystyrene resin used in the modified Merrifield techniques, by removal of the Fmoc group with piperidine/DMF and elimination of the resin with TFA/$CH_2Cl_2$(1:1)] in 15 ml of DMF is diluted with 85 ml of dichloromethane, and 50 mg of NaHCO$_3$ are added. After cooling in a dry ice/acetone mixture, 40 μl of diphenylphosphoryl azide are added. After standing at room temperature for 16 hours, the solution is concentrated. The concentrate is gel-filtered (Sephadex G10 column in isopropanol/water 8:2) and then purified by HPLC in the customary manner. Treatment with TFA/H$_2$O (98:2) gives cyclo-(NMe-Arg-Gly-Asp-D-Phe-Val); RT=18.1; FAB-MS (M+H): 589.

The following are obtained analogously by cyclization of the corresponding linear peptides and elimination of the protecting groups:

cyclo-(Arg-NMeGly-Asp-DPhe-Val); RT=17.9; FAB-MS (M+H): 589;
cyclo-(Arg-Gly-NMeAsp-DPhe-Val); RT=18.3; FAB-MS (M+H): 589;
cyclo-(Arg-Gly-NMeAsp-DPhe-Val)×TFA; RT=15.4; FAB-MS(M+H): 589;
cyclo-(Arg-Gly-Asp-NMeDPhe-Val); RT=18.9; FAB-MS (M+H): 589;
cyclo-(Arg-Gly-Asp-DPhe-NMeVal); RT=19.5; FAB-MS (M+H): 589;
cyclo-(Arg-Gly-Asp-DPhe-NMeLys); RT=11.1; FAB-MS (M+H): 618;
cyclo-(Arg-Gly-Asp-DPhe-NMeLys(benzyloxycarbonyl)× TFA=23.4; FAB-MS (M+H): 752;
cyclo-(NEtArg-Gly-Asp-DPhe-Val); FAB-MS (M+H): 603;
cyclo-(Arg-NEtGly-Asp-DPhe-Val); FAB-MS (M+H): 603;
cyclo-(Arg-Gly-NEtAsp-DPhe-Val); FAB-MS (M+H): 603;
cyclo-(Arg-Gly-Asp-NEtDPhe-Val); FAB-MS (M+H): 603;
cyclo-(Arg-Gly-Asp-DPhe-NEtVal); FAB-MS (M+H): 603;
cyclo-(Arg-Gly-Asp-DPhe(4-I)-NMeVal); RT=23.5; FAB-MS(M+H): 715;
cyclo-(NPrArg-Gly-Asp-DPhe-Val); FAB-MS (M+H): 617;
cyclo-(Arg-NPrGly-Asp-DPhe-Val); FAB-MS (M+H): 617;
cyclo-(Arg-Gly-NPrAsp-DPhe-Val); FAB-MS (M+H): 617;
cyclo-(Arg-Gly-Asp-NPrDPhe-Val); FAB-MS (M+H): 617;
cyclo-(Arg-Gly-Asp-DPhe-NPrVal); FAB-MS (M+H): 617;
cyclo-(NBzlArg-Gly-Asp-DPhe-Val); FAB-MS (M+H): 665;
cyclo-(Arg-NBzlGly-Asp-DPhe-Val); FAB-MS (M+H): 665;
cyclo-(Arg-Gly-NBzlAsp-DPhe-Val); FAB-MS (M+H): 665;
cyclo-(Arg-Gly-Asp-NBzlDPhe-Val); FAB-MS (M+H): 665;
cyclo-(Arg-Gly-Asp-DPhe-NBzlVal); FAB-MS (M+H): 665;
cyclo-(Arg-Gly-Asp-Phe-DNMeVal)x TFA; RT=18.2; FAB-MS(M+H): 589;
cyclo-(NMeArg-Gly-Asp-DPhe-Leu); FAB-MS (M+H): 603;
cyclo-(Arg-NMeGly-Asp-DPhe-Leu); FAB-MS (M+H): 603;
cyclo-(Arg-Gly-NMeAsp-DPhe-Leu); FAB-MS (M+H): 603;
cyclo-(Arg-Gly-Asp-NMeDPhe-Leu); FAB-MS (M+H): 603;
cyclo-(Arg-Gly-Asp-DPhe-NMeLeu); FAB-MS (M+H): 603;
cyclo-(NEtArg-Gly-Asp-DPhe-Leu); FAB-MS (M+H): 617;
cyclo-(Arg-NEtGly-Asp-DPhe-Leu); FAB-MS (M+H): 617;
cyclo-(Arg-Gly-NEtAsp-DPhe-Leu); FAB-MS (M+H): 617;
cyclo-(Arg-Gly-Asp-NEtDPhe-Leu); FAB-MS (M+H): 617;
cyclo-(Arg-Gly-Asp-DPhe-NEtLeu); FAB-MS (M+H): 617;
cyclo-(NPrArg-Gly-Asp-DPhe-Leu); FAB-MS (M+H): 631;
cyclo-(Arg-NPrGly-Asp-DPhe-Leu); FAB-MS (M+H): 631;
cyclo-(Arg-Gly-NPrAsp-DPhe-Leu); FAB-MS (M+H): 631;
cyclo-(Arg-Gly-Asp-NPrDPhe-Leu); FAB-MS (M+H): 631;
cyclo-(Arg-Gly-Asp-DPhe-NPrLeu); FAB-MS (M+H): 631;
cyclo-(NBzlArg-Gly-Asp-DPhe-Leu); FAB-MS (M+H): 679;
cyclo-(Arg-NBzlGly-Asp-DPhe-Leu); FAB-MS (M+H): 679;
cyclo-(Arg-Gly-NBzlAsp-DPhe-Leu); FAB-MS (M+H): 679;
cyclo-(Arg-Gly-Asp-NBzlDPhe-Leu); FAB-MS (M+H): 679;
cyclo-(Arg-Gly-Asp-DPhe-NBzlLeu); FAB-MS (M+H): 679;
cyclo-(NMeArg-Gly-Asp-DPhe-Ala);
cyclo-(Arg-NMeGly-Asp-DPhe-Ala);
cyclo-(Arg-Gly-NMeAsp-DPhe-Ala);
cyclo-(Arg-Gly-Asp-NMeDPhe-Ala);
cyclo-(Arg-Gly-Asp-DPhe-NMeAla); RT=16.2; FAB-MS (M+H): 561;
cyclo-(NEtArg-Gly-Asp-DPhe-Ala);
cyclo-(Arg-NEtGly-Asp-DPhe-Ala);
cyclo-(Arg-Gly-NEtAsp-DPhe-Ala);
cyclo-(Arg-Gly-Asp-NEtDPhe-Ala);
cyclo-(Arg-Gly-Asp-DPhe-NEtAla);
cyclo-(NPrArg-Gly-Asp-DPhe-Ala);
cyclo-(Arg-NPrGly-Asp-DPhe-Ala);
cyclo-(Arg-Gly-NPrAsp-DPhe-Ala);
cyclo-(Arg-Gly-Asp-NPrDPhe-Ala);
cyclo-(Arg-Gly-Asp-DPhe-NPrAla);
cyclo-(NBzlArg-Gly-Asp-DPhe-Ala);
cyclo-(Arg-NBzlGly-Asp-DPhe-Ala);
cyclo-(Arg-Gly-NBzlAsp-DPhe-Ala);
cyclo-(Arg-Gly-Asp-NBzlDPhe-Ala);
cyclo-(Arg-Gly-Asp-DPhe-NBzlAla);
cyclo-(NMeArg-Gly-Asp-DPhe-Gly);
cyclo-(Arg-NMeGly-Asp-DPhe-Gly);
cyclo-(Arg-Gly-NMeAsp-DPhe-Gly);
cyclo-(Arg-Gly-Asp-NMeDPhe-Gly);
cyclo-(Arg-Gly-Asp-DPhe-NMeGly); RT=14.3; FAB-MS (M+H): 547;
Cyclo-(DArg-Gly-Asp-DPhe-NMeVal)×TFA; RT=18.7; FAB-MS(M+H): 589;
cyclo-(NEtArg-Gly-Asp-DPhe-Gly);
cyclo-(Arg-NEtGly-Asp-DPhe-Gly);
cyclo-(Arg-Gly-NEtAsp-DPhe-Gly);
cyclo-(Arg-Gly-Asp-NEtDPhe-Gly);
cyclo-(Arg-Gly-Asp-DPhe-NEtGly);
cyclo-(NPrArg-Gly-Asp-DPhe-Gly);
cyclo-(Arg-NPrGly-Asp-DPhe-Gly);
cyclo-(Arg-Gly-NPrAsp-DPhe-Gly);
cyclo-(Arg-Gly-Asp-NPrDPhe-Gly);
cyclo-(Arg-Gly-Asp-DPhe-NPrGly);
cyclo-(NBzlArg-Gly-Asp-DPhe-Gly);
cyclo-(Arg-NBzlGly-Asp-DPhe-Gly);
cyclo-(Arg-Gly-NBzlAsp-DPhe-Gly);
cyclo-(Arg-Gly-Asp-NBzlDPhe-Gly);
cyclo-(Arg-Gly-Asp-DPhe-NBzlGly);
cyclo-(NMeArg-Gly-Asp-Phg-Val) (SEQ ID NO: 1);
cyclo-(Arg-NMeGly-Asp-Phg-Val) (SEQ ID NO: 2);
cyclo-(Arg-Gly-NMeAsp-Phg-Val) (SEQ ID NO: 3);
cyclo-(Arg-Gly-Asp-NMePhg-Val) (SEQ ID NO: 4);
cyclo-(Arg-Gly-Asp-Phg-NMeVal) (SEQ ID NO: 5);
cyclo-(NEtArg-Gly-Asp-Phg-Val) (SEQ ID NO: 6);
cyclo-(Arg-NEtGly-Asp-Phg-Val) (SEQ ID NO: 7);
cyclo-(Arg-Gly-NEtAsp-Phg-Val) (SEQ ID NO: 8);
cyclo-(Arg-Gly-Asp-NEtPhg-Val) (SEQ ID NO: 9);
cyclo-(Arg-Gly-Asp-Phg-NEtVal) (SEQ ID NO: 10);

cyclo-(NPrArg-Gly-Asp-Phg-Val) (SEQ ID NO: 11);
cyclo-(Arg-NPrGly-Asp-Phg-Val) (SEQ ID NO: 12);
cyclo-(Arg-Gly-NPrAsp-Phg-Val) (SEQ ID NO: 13);
cyclo-(Arg-Gly-Asp-NPrPhg-Val) (SEQ ID NO: 14);
cyclo-(Arg-Gly-Asp-Phg-NPrVal) (SEQ ID NO: 15);
cyclo-(NBzlArg-Gly-Asp-Phg-Val) (SEQ ID NO: 16);
cyclo-(Arg-NBzlGly-Asp-Phg-Val) (SEQ ID NO: 17);
cyclo-(Arg-Gly-NBzlAsp-Phg-Val) (SEQ ID NO: 18);
cyclo-(Arg-Gly-Asp-NBzlPhg-Val) (SEQ ID NO: 19);
cyclo-(Arg-Gly-Asp-Phg-NBzlVal) (SEQ ID NO: 20);
cyclo-(NMeArg-Gly-Asp-Trp-Val) (SEQ ID NO: 21);
cyclo- (Arg-NMeGly-Asp-Trp-Val) (SEQ ID NO: 22);
cyclo-(Arg-Gly-NMeAsp-Trp-Val) (SEQ ID NO: 23);
cyclo-(Arg-Gly-Asp-NMeTrp-Val) (SEQ ID NO: 24);
cyclo-(Arg-Gly-Asp-Trp-NMeVal) (SEQ ID NO: 25);
cyclo- (NEtArg-Gly-Asp-Trp-Val) (SEQ ID NO: 26);
cyclo-(Arg-NEtGly-Asp-Trp-Val) (SEQ ID NO: 27);
cyclo-(Arg-Gly-NEtAsp-Trp-Val) (SEQ ID NO: 28);
cyclo-(Arg-Gly-Asp-NEtTrp-Val) (SEQ ID NO: 29);
cyclo-(Arg-Gly-Asp-Trp-NEtVal) (SEQ ID NO: 30);
cyclo-(NPrArg-Gly-Asp-Trp-Val) (SEQ ID NO: 31);
cyclo-(Arg-NPrGly-Asp-Trp-Val) (SEQ ID NO: 32);
cyclo-(Arg-Gly-NPrAsp-Trp-Val) (SEQ ID NO: 33);
cyclo-(Arg-Gly-Asp-NPrTrp-Val) (SEQ ID NO: 34);
cyclo-(Arg-Gly-Asp-Trp-NPrVal) (SEQ ID NO: 35);
cyclo-(NBzlArg-Gly-Asp-Trp-Val) (SEQ ID NO: 36);
cyclo-(Arg-NBzGlyy-Asp-Trp-Val) (SEQ ID NO: 37);
cyclo-(Arg-Gly-NBzlAsp-Trp-Val) (SEQ ID NO: 38);
cyclo-(Arg-Gly-Asp-NBzlTrp-Val) (SEQ ID NO: 39);
cyclo-(Arg-Gly-Asp-Trp-NBzlVal) (SEQ ID NO: 40).

Example 2

A solution of 0.28 g of cyclo-(Arg(Mtr)-Gly-Asp-NMePhe-Dval) [obtainable by cyclization according to Ex. 1] in 8.4 ml of TFA, 1.7 ml of dichloromethane and 0.9 ml of thiophenol is allowed to stand at room temperature for 4 hours, then concentrated, and the residue is diluted with water and then freeze-dried. Gel filtration on Sephadex G 10 (acetic acid/water 1:1) and subsequent purification by preparative HPLC under the conditions indicated give cyclo-(Arg-Gly-Asp-NMePhe-DVal); FAB-MS (M+H): 589.

The following are obtained analogously:
from cyclo-(Arg(Mtr)-Gly-NMeAsp-DPhe-Ile): cyclo-(Arg-Gly-NMeAsp-DPhe-Ile); FAB-MS (M+H): 603;
from cyclo-(D-Arg(Mtr)-NMeGly-Asp(OBut)-DPhe-Nle): cyclo-(D-Arg-NMeGly-Asp-DPhe-Nle);
from cyclo-(NMeArg(Mtr)-Gly-D-Asp(OEt)-DPhe-Ile): cyclo-(NMeArg-Gly-D-Asp-DPhe-Ile);
from cyclo-(NMeArg(Mtr)-Gly-Asp-Phe-DIle): cyclo-(NMeArg-Gly-Asp-Phe-DIle);
from cyclo-(Arg(Mtr)-Gly-NMeAsp-Phe-DLeu): cyclo-(Arg-Gly-NMeAsp-Phe-DLeu);
from cyclo-(Arg(Mtr)-NMeGly-Asp-Phe-DSer): cyclo-(Arg-NMeGly-Asp-Phe-DSer);
from cyclo-(Arg(Mtr)-NMeGly-Asp-DNal-Leu): cyclo-(Arg-NMeGly-Asp-DNal-Leu);
from cyclo-(NMeArg(Mtr)-Gly-Asp-Nal-DIle): cyclo-(NMeArg-Gly-Asp-Nal-DIle);
from cyclo-(Arg(Mtr)-Gly-Asp-NMePhg-DVal): cyclo-(Arg-Gly-Asp-NMePhg-DVal);
from cyclo-(Arg(Mtr)-Gly-NMeAsp-Trp-DVal): cyclo-(Arg-Gly-NMeAsp-Trp-DVal).

Example 3

80 mg of cyclo-(Arg-Gly-Asp-DPhe-NMeVal) are dissolved in 0.01 m HCl five to six times and freeze-dried after each dissolving operation. Subsequent purification by HPLC gives cyclo-(Arg-Gly-Asp-DPhe-NMeVal)×HCl; FAB-MS (M+H): 589.

The following are obtained analogously:
from cyclo-(NMeArg-Gly-Asp-DPhe-Val): cyclo-(NMeArg-Gly-Asp-DPhe-Val):×HCl;
from cyclo-(Arg-NMeGly-Asp-DPhe-Val): cyclo-(Arg-NMeGly-Asp-DPhe-Val)×HCl; FAB-MS (M+H): 589;
from cyclo-(Arg-Gly-NMeAsp-DPhe-Val): cyclo-(Arg-Gly-NMeAsp-DPhe-Val)×HCl;
from cyclo-(Arg-Gly-Asp-NMeDPhe-Val): cyclo-(Arg-Gly-Asp-NMeDPhe-Val)×Hcl;
from cyclo-(Arg-Gly-Asp-Phe-DNMeVal): cyclo-(Arg-Gly-Asp-Phe-DNMeVal)×Hcl; RT=18.2; FAB-MS(M+H): 589.

Analogously the following is obtained by the treatment with acetic acid (AcOH):
from cyclo-(Arg-Gly-NMeAsp-DPhe-Val): cyclo-(Arg-Gly-NMeAsp-DPhe-Val)×AcOH; RT=15.4; FAB-MS(M+H): 589.

Analogously the following is obtained by the treatment with methane sulfonic acid ($MeSO_3H$):
from cyclo-(Arg-Gly-Asp-DPhe-NMeVal): cyclo-(Arg-Gly-Asp-DPhe-NMeVal)×$MeSO_3H$; RT=17,8; FAB-MS(M+H): 589;

Example 4

To prepare affinity phases, 0.9 g of N-maleimido-$(CH_2)_5$—CO—NH—$(CH_2)_3$ polymer [obtainable by condensation of N-maleimido-$(CH_2)_5$—COOH with $H_2N$—$(CH_2)_3$ polymer] is suspended in 10 ml of 0.1 M sodium phosphate buffer at a pH of 7, and one equivalent cyclo-(Arg-Gly-Asp-DPhe-NMeLys($CO(CH_2)_2SH$) is added at 4°. The reaction mixture is stirred for 4 hours with simultaneous warming to room temperature, and the solid residue is filtered off and washed twice with 10 ml each of buffer solution (pH 7) and then three times with 10 ml each time of water. Cyclo-(Arg-Gly-Asp-DPhe-NMeLys $(CO(CH_2)_2S$-3-(N-maleimido-$(CH_2)_5$—CONH—$(CH_2)_3$ polymer)) is obtained.

Example 5

Analogously to Example 4, condensation of polymer-O-$(CH_2)_3$—$NH_2$ [commercially available] and cyclo-(Arg-Gly-Asp-NMe-DPhe-Lys($CO(CH_2)_4COOH$) [obtainable by condensing adipic acid with cyclo-(Arg-Gly-Asp-NMe-DPhe-Lys) under the stated conditions] gives the following polymeric phase: cyclo-(Arg-Gly-Asp-NMe-DPhe-Lys-(CO—$(CH_2)_4$—CO—NH—$(CH_2)_3$—O-polymer)

The following is obtained analogously by condensation of:
cyclo-(NMe-Arg-Gly-Asp-DPhe-Lys-(CO—$(CH_2)_5$—$NH_2$)) with HOOC—$CH_2$—O-polymer:
cyclo-(NMe-Arg-Gly-Asp-DPhe-Lys-(CO—$(CH_2)_5$—NH—CO—$CH_2$—O-polymer)).

The following examples relate to pharmaceutical preparations.

Example A

Injection Vials

A solution of 100 g of a cyclopeptide of the formula I and 5 g of disodium hydrogen phosphate in 3 1 of double-distilled water is adjusted to a pH of 6.5 with 2 n hydrochloric acid, subjected to sterile filtration, dispensed into injection vials and lyophilized under sterile conditions, and the vials are sealed in a sterile manner. Each injection vial contains 5 mg of active principle.

Example B
Suppositories

A mixture of 20 g of active principle of the formula I is melted with 100 g of soya lecithin and 1400 g of cocoa butter, and the mixture is poured into molds and allowed to cool. Each suppository contains 20 mg of active principle.

Example C
Solution

A solution is prepared from 1 g of active principle of the formula I, 9.38 g of $NaH_2PO_4 \times 2\ H_2O$, 28.48 g of $Na_2HPO_4 \times 12\ H_2O$ and 0.1 g of benzalkonium chloride in 940 ml of double-distilled water. The pH is adjusted to 6.8, the solution is made up to 1 l and is sterilized by irradiation. This solution can be used in the form of eye drops.

Example D
Ointment 500 mg of active principle of the formula I are mixed with 99.5 g of petroleum jelly under aseptic conditions.

Example E
Tablets

A mixture of 100 g of a cyclopeptide of the formula I, 1 kg of lactose, 600 g of microcrystallized cellulose, 600 g of maize starch, 100 g of polyvinylpyrrolidone, 80 g of talc and 10 g of magnesium stearate is pressed to give tablets in a customary manner, such that each tablet contains 10 mg of active principle.

Example F
Coated Tablets

Tablets are pressed as stated in Example E and are then coated in a customary manner with a coating of sucrose, maize starch, talc, tragacanth and colorant.

Example G
Capsules

Hard gelatin capsules are filled in a customary manner with an active principle of the formula I such that each capsule contains 5 mg of active principle.

Example H
Inhalation Spray 14 g of active principle of the formula I are dissolved in 10 l of isotonic NaCl solution, and the solution is used to fill commercially available spray canisters having a pump mechanism. The solution can be sprayed into the mouth or nose. One spray burst (about 0.1 ml) corresponds to a dose of about 0.14 mg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

---

What is claimed is:

1. A compound of the formula cyclo-(Arg-Gly-Asp-DPhe-NMeVal), including both the D and L forms of optically active amino acids, or a physiologically acceptable salt thereof.

2. An enantiomer or diastereomer of the compound of claim 1.

3. A compound according to claim 1, further comprising a fluorescent substituent.

4. A pharmaceutical composition comprising a compound according to claim 1, or a physiologically acceptable salt thereof, and a pharmaceutically acceptable carrier.

5. A process for the production of a pharmaceutical preparation, comprising compounding a compound according to claim 1, or a physiologically acceptable salt thereof, into an appropriate dosage form together with at least one solid, liquid or semi-liquid excipient or auxiliary.

* * * * *

```
                        SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
         (A) LENGTH: 5 amino acids
         (B) TYPE: amino acid
         (D) TOPOLOGY: circular (ii) MOLECULE TYPE: peptide (ix) FEATURE:
         (A) NAME/KEY: Modified-site
         (B) LOCATION:1
         (D) OTHER INFORMATION:/product= "NMeArg"

(ix) FEATURE:
         (A) NAME/KEY: Modified-site
         (B) LOCATION:4
         (D) OTHER INFORMATION:/product= "Phenylglycine"

(xi) SEQUENCE DESCRIPTION: SEQ ID NO:1:

Arg Gly Asp Xaa Val
   1               5

(2) INFORMATION FOR SEQ ID NO:2:

(i) SEQUENCE CHARACTERISTICS:
         (A) LENGTH: 5 amino acids
         (B) TYPE: amino acid
         (D) TOPOLOGY: circular (ii) MOLECULE TYPE: peptide (ix) FEATURE:
```

```
            (A) NAME/KEY: Modified-site
            (B) LOCATION:2
            (D) OTHER INFORMATION:/product= "NMeGly"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:2:

Arg Gly Asp Xaa Val
1               5

(2) INFORMATION FOR SEQ ID NO:3:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:3
            (D) OTHER INFORMATION:/product= "NMeAsp"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:3:

Arg Gly Asp Xaa Val
1               5

(2) INFORMATION FOR SEQ ID NO:4:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:4
            (D) OTHER INFORMATION:/product= "NMePhenylglycine"

(xi) SEQUENCE DESCRIPTION: SEQ ID NO:4:

Arg Gly Asp Xaa Val
1               5

(2) INFORMATION FOR SEQ ID NO:5:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:5
            (D) OTHER INFORMATION:/product= "NMeVal"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:5:
```

```
Arg Gly Asp Xaa Val
1               5

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NEtArg"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:6:

Arg Gly Asp Xaa Val
1               5

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NEtGly"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:7:

Arg Gly Asp Xaa Val
1               5

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NEtAsp"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:8:

Arg Gly Asp Xaa Val
1               5
```

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NEtPhenylglycine"

(xi) SEQUENCE DESCRIPTION: SEQ ID NO:9:

Arg Gly Asp Xaa Val
1               5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NEtVal"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:10:

Arg Gly Asp Xaa Val
1               5

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NPrArg"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:11:

Arg Gly Asp Xaa Val
1               5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:

(A) NAME/KEY: Modified-site
            (B) LOCATION:2
            (D) OTHER INFORMATION:/product= "NPrGly"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:12:

Arg Gly Asp Xaa Val
1               5

(2) INFORMATION FOR SEQ ID NO:13:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:3
            (D) OTHER INFORMATION:/product= "NPrAsp"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:13:

Arg Gly Asp Xaa Val
1               5

(2) INFORMATION FOR SEQ ID NO:14:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:4
            (D) OTHER INFORMATION:/product= "NPrPhenylglycine"

(xi) SEQUENCE DESCRIPTION: SEQ ID NO:14:

Arg Gly Asp Xaa Val
1               5

(2) INFORMATION FOR SEQ ID NO:15:

(i) SEQUENCE CHARACTERISTICS:
            (A) LENGTH: 5 amino acids
            (B) TYPE: amino acid
            (D) TOPOLOGY: circular (ii) MOLECULE TYPE: peptide (ix) FEATURE:
            (A) NAME/KEY: Modified-site
            (B) LOCATION:5
            (D) OTHER INFORMATION:/product= "NPrVal"

(ix) FEATURE:
            (A) NAME/KEY: Modified-site
            (B) LOCATION:4
            (D) OTHER INFORMATION:/product= "Phenylglycine"

(xi) SEQUENCE DESCRIPTION: SEQ ID NO:15:

```
Arg Gly Asp Xaa Val
 1               5
```

(2) INFORMATION FOR SEQ ID NO:16:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NBzlArg"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:16:

```
Arg Gly Asp Xaa Gly
 1               5
```

(2) INFORMATION FOR SEQ ID NO:17:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NBzlGly"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:17:

```
Arg Gly Asp Xaa Val
 1               5
```

(2) INFORMATION FOR SEQ ID NO:18:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NBzlAsp"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:18:

```
Arg Gly Asp Xaa Val
 1               5
```

(2) INFORMATION FOR SEQ ID NO:19:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NBzlPhenylglycine"

(xi) SEQUENCE DESCRIPTION: SEQ ID NO:19:

Arg Gly Asp Xaa Val
1           5

(2) INFORMATION FOR SEQ ID NO:20:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NBzlVal"

(ix) FEATURE:
        (A) NAME/KEY: Modified-site
        (B) LOCATION:4
        (D) OTHER INFORMATION:/product= "Phenylglycine"

(xi) SEQUENCE DESCRIPTION: SEQ ID NO:20:

Arg Gly Asp Xaa Val
1           5

(2) INFORMATION FOR SEQ ID NO:21:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NMeArg"

(xi) SEQUENCE DESCRIPTION: SEQ ID NO:21:

Arg Gly Asp Trp Gly
1           5

(2) INFORMATION FOR SEQ ID NO:22:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NMeGly"

(xi) SEQUENCE DESCRIPTION: SEQ ID NO:22:

Arg Gly Asp Trp Val
1               5

(2) INFORMATION FOR SEQ ID NO:23:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NMeAsp"

(xi) SEQUENCE DESCRIPTION: SEQ ID NO:23:

Arg Gly Asp Trp Val
1               5

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NMeTrp"

(xi) SEQUENCE DESCRIPTION: SEQ ID NO:24:

Arg Gly Asp Trp Val
1               5

(2) INFORMATION FOR SEQ ID NO:25:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NMeVal"

(xi) SEQUENCE DESCRIPTION: SEQ ID NO:25:

Arg Gly Asp Trp Val
1               5

(2) INFORMATION FOR SEQ ID NO:26:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NEtArg"

(xi) SEQUENCE DESCRIPTION: SEQ ID NO:26:

Arg Gly Asp Trp Gly
1               5

(2) INFORMATION FOR SEQ ID NO:27:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NEtGly"

(xi) SEQUENCE DESCRIPTION: SEQ ID NO:27:

Arg Gly Asp Trp Val
1               5

(2) INFORMATION FOR SEQ ID NO:28:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NEtAsp"

(xi) SEQUENCE DESCRIPTION: SEQ ID NO:28:

Arg Gly Asp Xaa Val
1               5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NEtTrp"

(xi) SEQUENCE DESCRIPTION: SEQ ID NO:29:

Arg Gly Asp Trp Val
1               5

(2) INFORMATION FOR SEQ ID NO:30:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NEtVal"

(xi) SEQUENCE DESCRIPTION: SEQ ID NO:30:

-continued

Arg Gly Asp Trp Val
1               5

(2) INFORMATION FOR SEQ ID NO:31:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NPrArg"

(xi) SEQUENCE DESCRIPTION: SEQ ID NO:31:

Arg Gly Asp Trp Gly
1               5

(2) INFORMATION FOR SEQ ID NO:32:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NPrGly"

(xi) SEQUENCE DESCRIPTION: SEQ ID NO:32:

Arg Gly Asp Trp Val
1               5

(2) INFORMATION FOR SEQ ID NO:33:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NPrAsp"

(xi) SEQUENCE DESCRIPTION: SEQ ID NO:33:

Arg Gly Asp Trp Val
1               5

(2) INFORMATION FOR SEQ ID NO:34:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NPrTrp"

(xi) SEQUENCE DESCRIPTION: SEQ ID NO:34:

Arg Gly Asp Trp Val
1               5

(2) INFORMATION FOR SEQ ID NO:35:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NPrVal"

(xi) SEQUENCE DESCRIPTION: SEQ ID NO:35:

Arg Gly Asp Trp Val
1               5

(2) INFORMATION FOR SEQ ID NO:36:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:1
        (D) OTHER INFORMATION:/product= "NBzlArg"

(xi) SEQUENCE DESCRIPTION: SEQ ID NO:36:

Arg Gly Asp Trp Gly
1               5

(2) INFORMATION FOR SEQ ID NO:37:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:2
        (D) OTHER INFORMATION:/product= "NBzlGly"

(xi) SEQUENCE DESCRIPTION: SEQ ID NO:37:

Arg Gly Asp Trp Val
1               5

(2) INFORMATION FOR SEQ ID NO:38:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:3
        (D) OTHER INFORMATION:/product= "NBzlAsp"

(xi) SEQUENCE DESCRIPTION: SEQ ID NO:38:

```
Arg Gly Asp Trp Val
1               5

(2) INFORMATION FOR SEQ ID NO:39:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:4
        (D) OTHER INFORMATION:/product= "NBzlTrp"

(xi) SEQUENCE DESCRIPTION: SEQ ID NO:39:

Arg Gly Asp Trp Val
1               5

(2) INFORMATION FOR SEQ ID NO:40:

(i) SEQUENCE CHARACTERISTICS:
        (A) LENGTH: 5 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION:5
        (D) OTHER INFORMATION:/product= "NBzlVal"

(xi) SEQUENCE DESCRIPTION: SEQ ID NO:40:

Arg Gly Asp Trp Val
1               5
```